(12) United States Patent
Hutchful

(10) Patent No.: US 10,568,769 B2
(45) Date of Patent: Feb. 25, 2020

(54) FABRIC SLEEVES COVERING TOE AND FINGER BLEMISHES AND TREATING SAID BLEMISHES

(71) Applicant: Evadne I. Hutchful, Las Vegas, NV (US)

(72) Inventor: Evadne I. Hutchful, Las Vegas, NV (US)

( * ) Notice: Subject to any disclaimer, the term of this patent is extended or adjusted under 35 U.S.C. 154(b) by 277 days.

(21) Appl. No.: 15/499,219

(22) Filed: Apr. 27, 2017

(65) Prior Publication Data

US 2017/0340486 A1    Nov. 30, 2017

Related U.S. Application Data

(60) Provisional application No. 62/392,325, filed on May 27, 2016.

(51) Int. Cl.

| *A61F 13/00* | (2006.01) |
|---|---|
| *A61F 13/06* | (2006.01) |
| *A61F 13/10* | (2006.01) |

(52) U.S. Cl.
CPC .. *A61F 13/00059* (2013.01); *A61F 13/00017* (2013.01); *A61F 13/00063* (2013.01); *A61F 13/00072* (2013.01); *A61F 13/00085* (2013.01); *A61F 13/068* (2013.01); *A61F 13/105* (2013.01); *A61F 2013/0028* (2013.01); *A61F 2013/00093* (2013.01); *A61F 2013/00285* (2013.01)

(58) Field of Classification Search
CPC ................. A61F 13/063; A61F 13/068; A61F 2013/0048; A61F 13/00059; A61F 2013/0093; A61F 13/00085; A61F 13/105; A61F 13/06; A61F 13/065; A61F 13/069; A61F 13/10
See application file for complete search history.

(56) References Cited

U.S. PATENT DOCUMENTS

| 2,044,523 A | * | 6/1936 | Bertram | A61F 13/063 128/894 |
|---|---|---|---|---|
| 2,389,831 A | * | 11/1945 | Welsh | A61F 13/105 2/21 |
| 2,567,926 A | * | 9/1951 | Dunkelberger | A61F 6/04 128/844 |
| 2,571,946 A | * | 10/1951 | Rosenfield | A61F 13/105 602/1 |
| 5,181,914 A | * | 1/1993 | Zook | A61F 13/105 128/888 |

(Continued)

*Primary Examiner* — Matthew F Desanto

(57) ABSTRACT

A system is provided comprising a columnar sleeve of stretchable fabric, the sleeve produced in various skin tone colors and configured to slip upon an individual toe or finger and an absorbent padding configured for attachment to an inside surface of the sleeve, the padding configured to cover about one half of an interior circumference of the inside surface, the padding optionally infused with at least one of pain killers, antiseptics, and soothing gels. The system also comprises wax paper covering the padding prior to use of the sleeve, an applicator shaped to facilitate slipping the sleeve upon the individual toe or finger, and convex-shaped flex bands placed lengthwise into the sleeve. The flex bands exert downward pressure on one of a toe and a finger and are placed in a U-shape, thus promoting the downward pressure.

19 Claims, 6 Drawing Sheets

(56) References Cited

U.S. PATENT DOCUMENTS

| | | | | |
|---|---|---|---|---|
| 5,497,789 | A * | 3/1996 | Zook | A61F 13/063 |
| | | | | 128/893 |
| 5,499,966 | A * | 3/1996 | Bulley | A61F 5/05875 |
| | | | | 602/41 |
| 7,552,501 | B2 * | 6/2009 | Yang | A45D 34/04 |
| | | | | 15/227 |
| 9,968,143 | B2 * | 5/2018 | Martin | A41D 13/087 |
| 2002/0095107 | A1 * | 7/2002 | Martin | A61F 13/06 |
| | | | | 602/61 |
| 2002/0169404 | A1 * | 11/2002 | Olderr | A61F 13/068 |
| | | | | 602/41 |
| 2008/0071206 | A1 * | 3/2008 | Peters | A61F 13/10 |
| | | | | 602/41 |
| 2008/0262403 | A1 * | 10/2008 | Martin | A41D 13/087 |
| | | | | 602/63 |
| 2009/0105625 | A1 * | 4/2009 | Kohner | A61F 13/068 |
| | | | | 602/54 |
| 2009/0126413 | A1 * | 5/2009 | Sorensen | A61F 13/04 |
| | | | | 66/196 |
| 2014/0135676 | A1 * | 5/2014 | De Man | A61F 13/00029 |
| | | | | 602/43 |

* cited by examiner

FABRIC SLEEVES COVERING TOE AND FINGER BLEMISHES AND TREATING SAID BLEMISHES

CROSS-REFERENCE TO RELATED APPLICATIONS

The present Utility patent application claims priority benefit of the U.S. provisional application for patent Ser. No. 62/392,325 filed 27 May 2016 under 35 U.S.C. 119(e). The contents of this related provisional application are incorporated herein by reference for all purposes to the extent that such subject matter is not inconsistent herewith or limiting hereof.

RELATED CO-PENDING U.S. PATENT APPLICATIONS

Not applicable.

INCORPORATION BY REFERENCE OF SEQUENCE LISTING PROVIDED AS A TEXT FILE

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to an apparatus for covering and protecting human body blemishes. More particularly, certain embodiments of the invention relate to a seamless, stretchable fabric sleeve infused with medications, pain killers, antiseptics and soothing gels, the sleeve producible in a variety of skin tone and other colors and designs and for use in rolling onto a human finger or toe to cover blemishes, whereby a plurality of sleeves in rolled state prior to use may be stored on a cylinder, the cylinder attachable to a cone-shaped applicator the fits over an affected toe or finger and facilitating placement of the sleeve thereon.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that persons often seek to wear open toe footwear such as sandals, flip flops and peep-toes in casual settings. However, such persons may be reluctant to do so because of unsightly and perhaps painful callouses, corns, bunions, warts, blisters and other conditions openly visible on their toes. Persons may also have blisters and other imperfections on their fingers which they consider unsightly. Particularly in warm weather, individuals may wish to wear such footwear that exposes toes to open air. Such individuals seek ways to safely conceal such imperfections on their skin such that they may enjoy the comfort and fashion of many types of open toe footwear. Further, exposed calluses, corns and blisters may suffer further injury when openly exposed and may ooze blood and other bodily fluids that may stain clothing, furniture, carpeting and automobile interiors.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
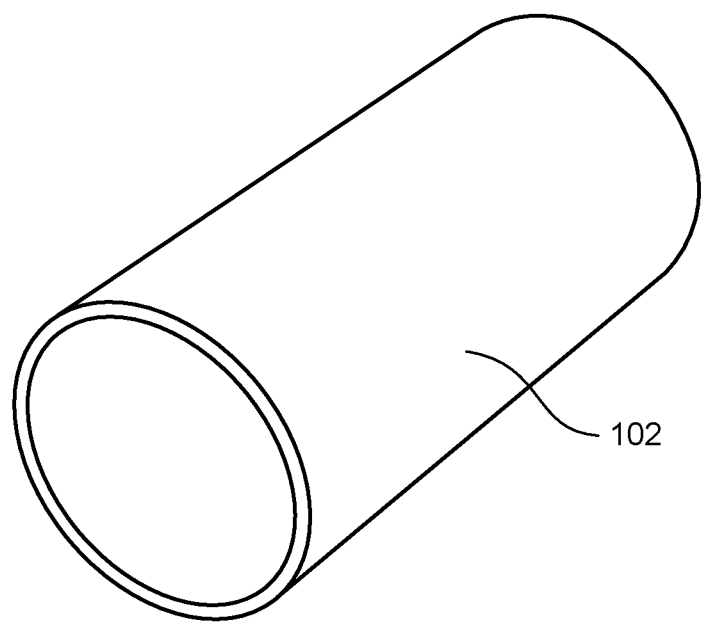
FIG. 1 is a diagram depicting an unrolled unit of the fabric sleeve in accordance with an embodiment of the present disclosure, the sleeve covering a blemish on a toe or finger of wearer, this depiction representing the fabric sleeve at its simplest with no padding or flex bands.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settle law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognize in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that, that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" includes the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of, or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising." This term is open-ended. As used in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. .sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of" where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation of any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

The present invention will now be described in detail with reference to embodiments thereof as illustrated in the accompanying drawings.

There are various types of designs for protection of blemishes of various kinds on toes and fingers. In embodiments of the present disclosure, a kit is provided to conceal blemishes including corns, calluses, warts, scars and blisters on toes and fingers. The kit includes stretchable fabric sleeves that may be slipped over a toe or finger to conceal such blemishes. A storage cylinder hosts rolled units of the fabric sleeves prior to use. A cone-shaped applicator that fits over the toe or finger connects to the cylinder and facilitates rolling the sleeve onto the toe or finger.

The sleeve is seamless and columnar and made of stretchable fabric produced in various skin colors. The seamless aspect may ensure that the sleeve is comfortable to wear, such that nothing pokes into the toe or finger that might cause discomfort. The skin tone color helps to disguise and camouflage the use of the product.

The interior of the fabric sleeve may host absorbent padding. The padding may be as long as the fabric sleeve and cover one half of the interior circumference of the sleeve. The padding may make having a toe blemish more comfortable. The padding cushions and protects blemishes and may absorb blood or other bodily fluid excreting from such blemishes. The padding may be infused with medications, pain killers, antiseptics, and soothing gels.

The padding is protected by wax paper prior to use of the sleeve. The wax paper features an extending tab to allow the user to grip the wax paper and remove it from the sleeve.

Convex-shaped flex bands may be integrated lengthwise into the sleeve. The flex bands may be in parallel alignment to one another. Their convex shape causes downward pressure that may help stop bleeding and reduce or eliminate the bulging puffiness of blemishes. Some toe blemishes that are associated with compact toe bones may be relieved and possibly healed by this downward pressure.

FIG. 1 is a diagram depicting an unrolled unit of the fabric sleeve 102 in accordance with an embodiment of the present disclosure, the sleeve 102 covering a blemish on a toe or finger of wearer, this depiction representing the fabric sleeve at its simplest with no padding or flex bands. FIG. 1 depicts sleeve 102 in an unrolled state as it encases, envelopes or surrounds the toe or finger and conceals the blemish. The sleeve 102 as depicted may be in its simplest version with no padding or flex bands. The sleeve 102 is seamless and with no hems and may contain padding infused with medicating substances.

Figure 2:
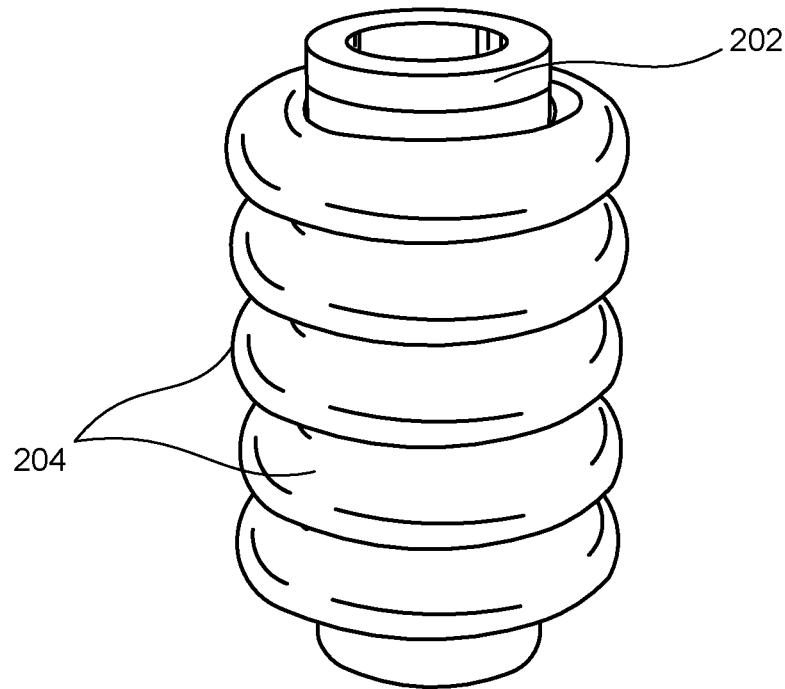
FIG. 2 is a diagram depicting several rolled units of the fabric sleeve in accordance with an embodiment of the present disclosure, the rolled sleeves stored on a cylinder and awaiting placement via unrolling onto one of a finger and toe.

FIG. 2 is a diagram depicting several rolled units 204 of the fabric sleeve 102 in accordance with an embodiment of the present disclosure, the rolled sleeves 204 stored on a cylinder 202 and awaiting placement via unrolling onto one of a finger and toe. The cylinder 202 is constructed so that it joins with the cone-shaped applicator such that the fabric sleeve can be rolled from the cylinder 202 over the applicator and onto the toe or finger.

Figure 3:
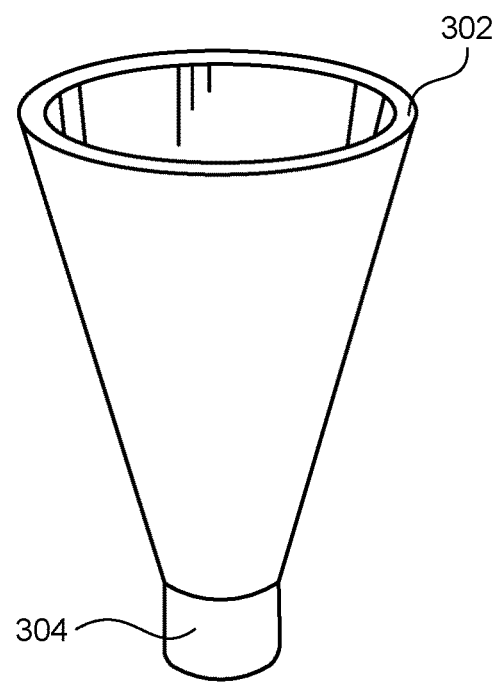
FIG. 3 is a diagram depicting a cone-shaped applicator in accordance with an embodiment of the present disclosure for use in fitting over a finger or toe in rolling the fabric sleeve onto the finger or toe, the application having a narrow shape at an end away from the finger or toe designed to fit directly into the end of the storage cylinder.

FIG. 3 is a diagram depicting a cone-shaped applicator 302 in accordance with an embodiment of the present disclosure for use in fitting over a finger or toe in rolling the fabric sleeve 102 onto the finger or toe. The applicator 302 having a narrow shape at an end 304 away from the finger or toe designed to fit directly into the end of the storage cylinder 202.

Figure 4:
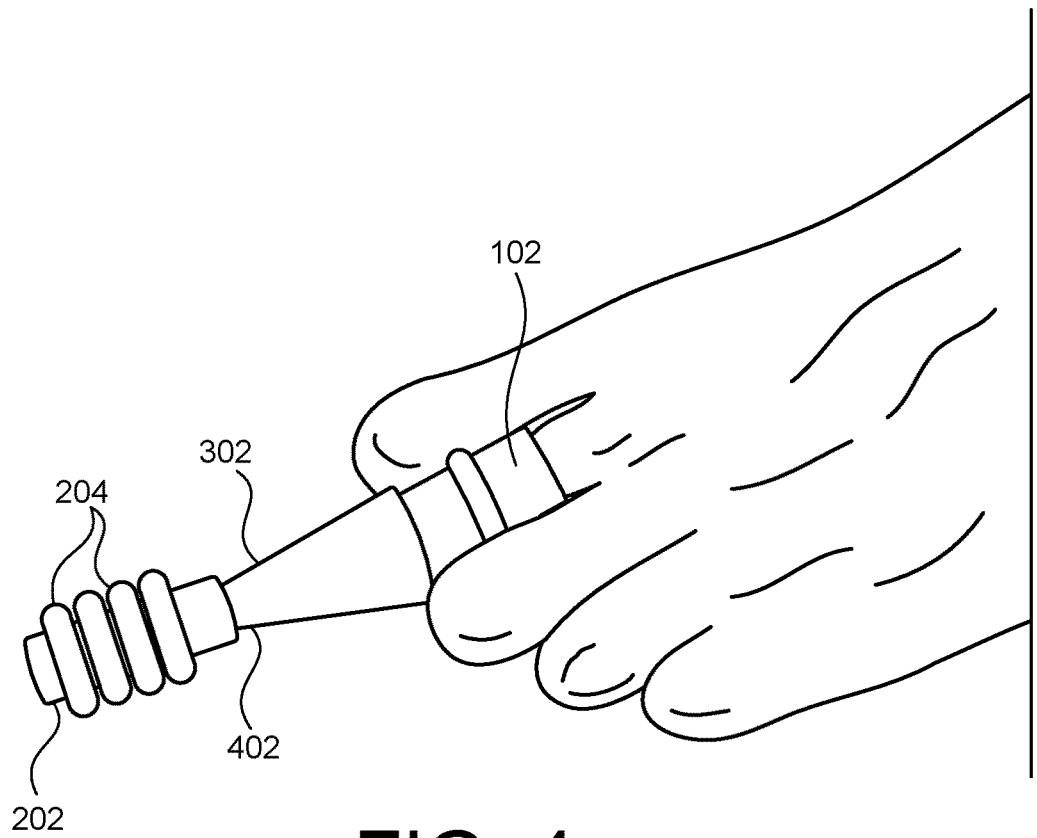
FIG. 4 is a diagram depicting the cylinder in accordance with an embodiment of the present disclosure, which stores a plurality of rolled units, joined with the cone-shaped applicator in a manner that promotes ease of transfer of rolled sleeves from cylinder to applicator, FIG. 4 also depicting the applicator covering a human toe with a sleeve that has been rolled onto toe from cylinder via the applicator, the sleeve depicted as partially unrolled on the affected toe.

FIG. 4 is a diagram depicting the cylinder 202 in accordance with an embodiment of the present disclosure, which stores a plurality of rolled units 204, joined with the cone-shaped applicator 302 in a manner that promotes ease of transfer of rolled sleeves 204 from cylinder 202 to applicator 302. FIG. 4 also depicts the applicator 302 covering a human toe with a sleeve 102 that has been rolled onto the toe from the cylinder 202 via the applicator 302, the sleeve 102 depicted as partially unrolled onto the affected toe.

Figure 5:
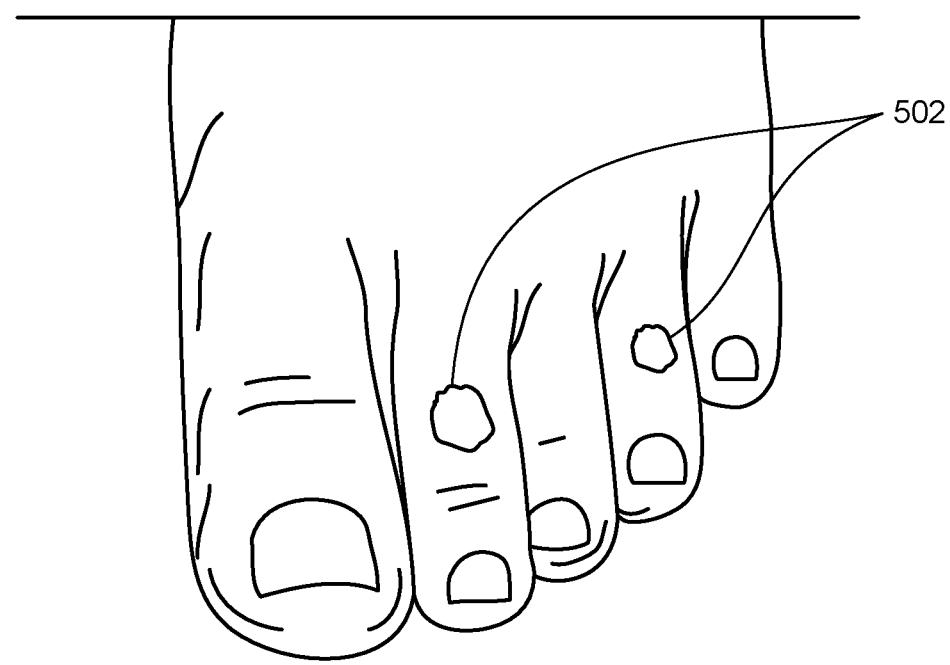
FIG. 5 is an image of a human foot and toes with visible toe blemishes in accordance with an embodiment of the present disclosure.

FIG. 5 is an image of a human foot and toes with visible toe blemishes in accordance with an embodiment of the present disclosure. The blemishes may be warts, corns, or other foot ailments.

Figure 6:
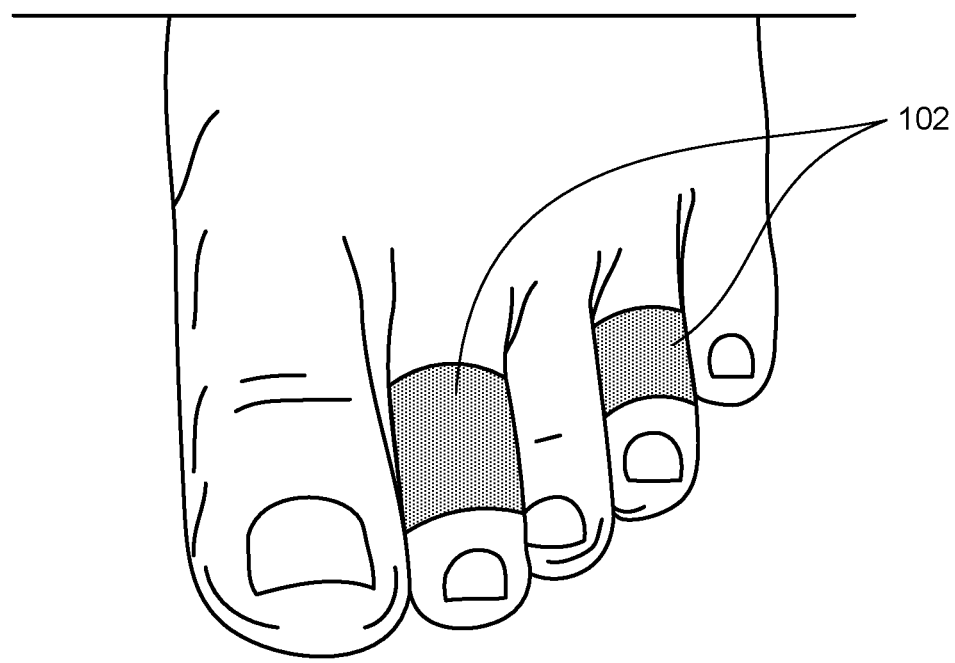
FIG. 6 is an image of a human foot and toes with skin-toned fabric sleeves completely covering and camouflaging toe blemishes in accordance with an embodiment of the present disclosure.

FIG. 6 is an image of a human foot and toes with skin-toned fabric sleeves 102 completely covering and camouflaging toe blemishes in accordance with an embodiment of the present disclosure. As noted, sleeves 102 may come in various skin tones to assist in concealing blemishes and blending in with the user's natural skin tone.

Figure 7:
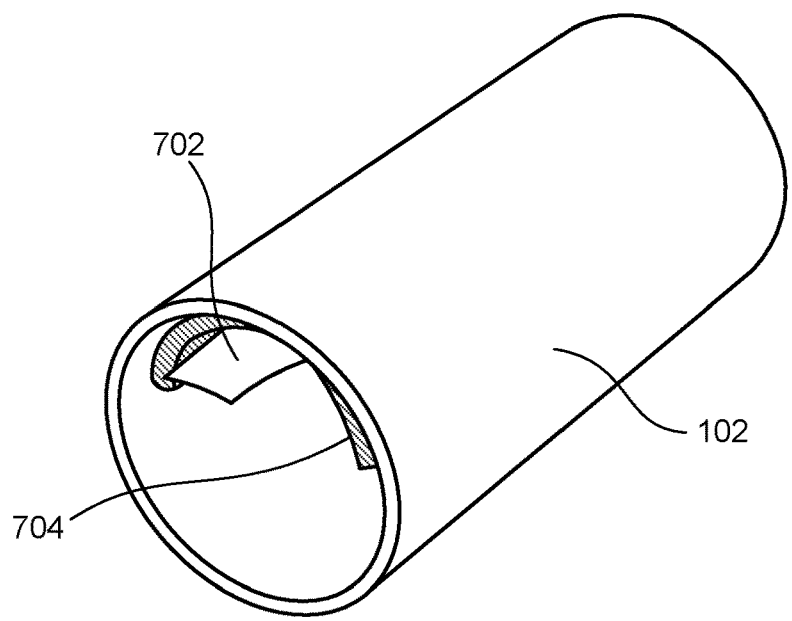
FIG. 7 is a diagram depicting a pull tab of wax paper covering absorbent padding adhered to an inside surface of the fabric sleeve in accordance with an embodiment of the present disclosure.

FIG. 7 is a diagram depicting a pull tab 702 of wax paper covering absorbent padding 704 adhered to an inside surface of the fabric sleeve 102 in accordance with an embodiment of the present disclosure. The wax paper covers the padding 704 until the fabric sleeve 102 is ready to be used.

Figure 8:
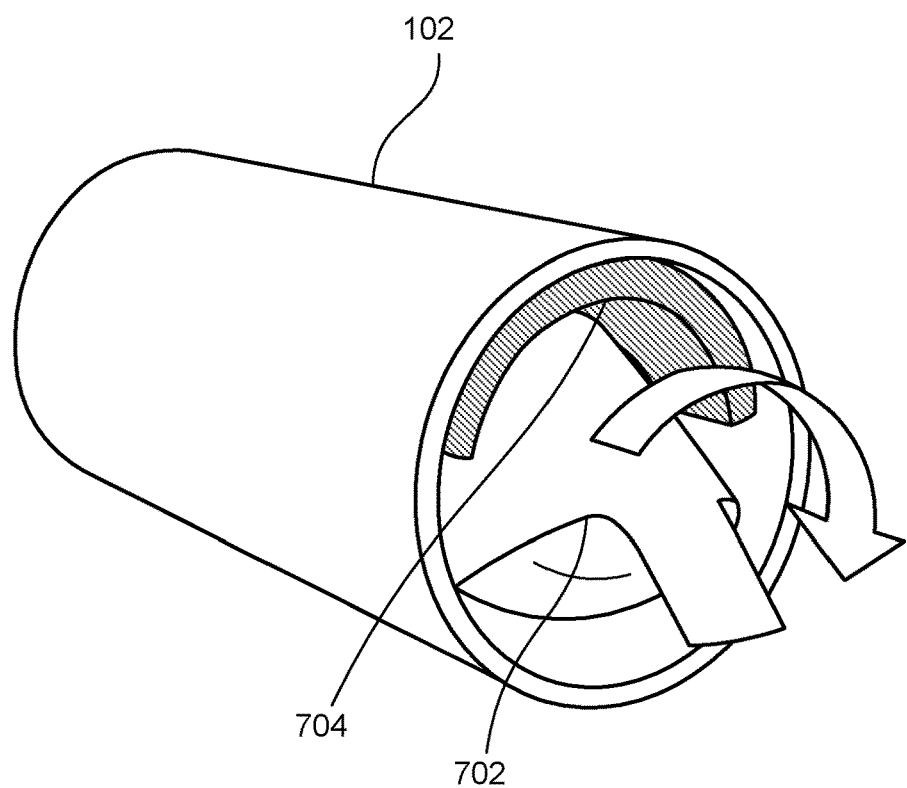
FIG. 8 is a diagram depicting, in accordance with an embodiment of the present disclosure, the pull tab of wax paper being removed from its position covering absorbent padding, the padding adhered to the inside surface of the fabric sleeve.

FIG. 8 is a diagram depicting, in accordance with an embodiment of the present disclosure, the pull tab 702 of wax paper being removed from its position covering absorbent padding 704, the padding 704 adhered to the inside surface of the fabric sleeve 102. The arrow depicted shows the manner in which the pull tab 702 is pulled for removal.

Figure 9:
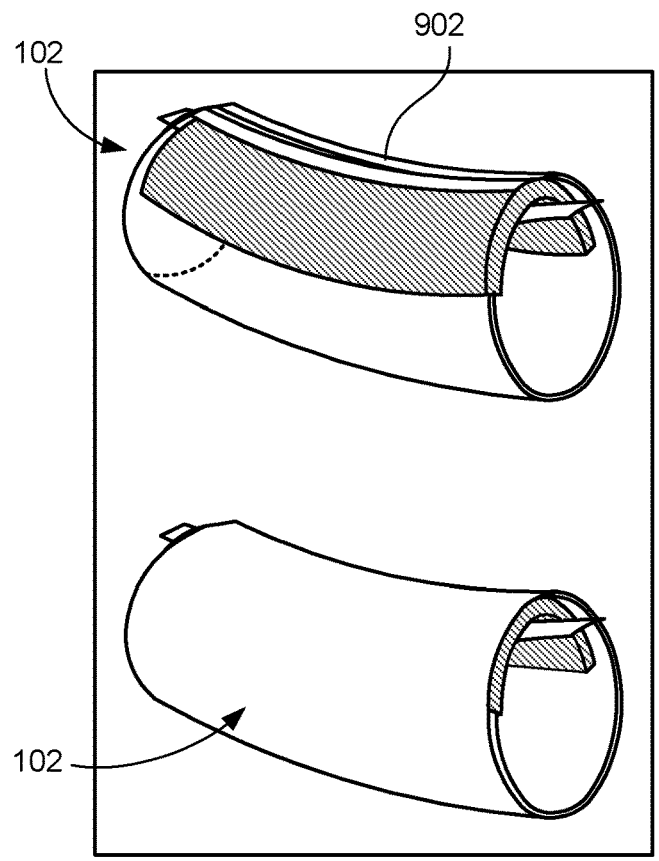
FIG. 9 is a diagram depicting, in accordance with an embodiment of the present disclosure, a transparent view of the fabric sleeve in unrolled state with flex bands and padding, and further depicting a non-transparent view with the fabric sleeve bent in a slight U-shape based on action of the flex bands.

FIG. 9 is a diagram depicting, in accordance with an embodiment of the present disclosure, a transparent view of the fabric sleeve 102 in unrolled state with flex bands 902 and padding 704, and further depicting a non-transparent view with the fabric sleeve 102 bent in a slight U-shape based on action of the flex bands 902. The flex bands 902 may be used to manipulate the shape of the sleeve 102 such that appropriate pressure is placed against blemishes. The flex bands 902 are an important component of the present disclosure as placing pressure against affected areas may be vital in supporting recovery from toe and finger problems.

Figure 10:
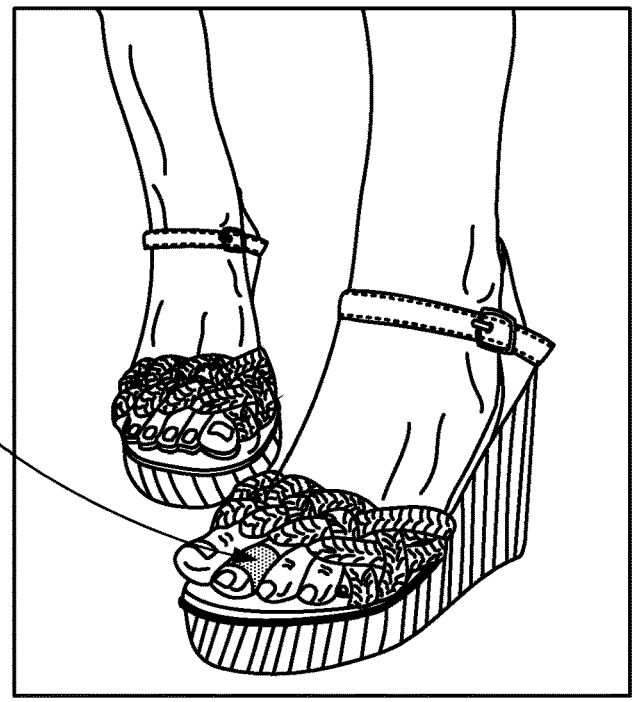
FIG. 10 is a photographic image of a fabric sleeve covering a toe blemish on a person wearing open-toe footwear in accordance with an embodiment of the present disclosure.

FIG. 10 is a photographic image of a fabric sleeve 102 covering a toe blemish on a person wearing open-toe footwear in accordance with an embodiment of the present disclosure.

Figure 11:
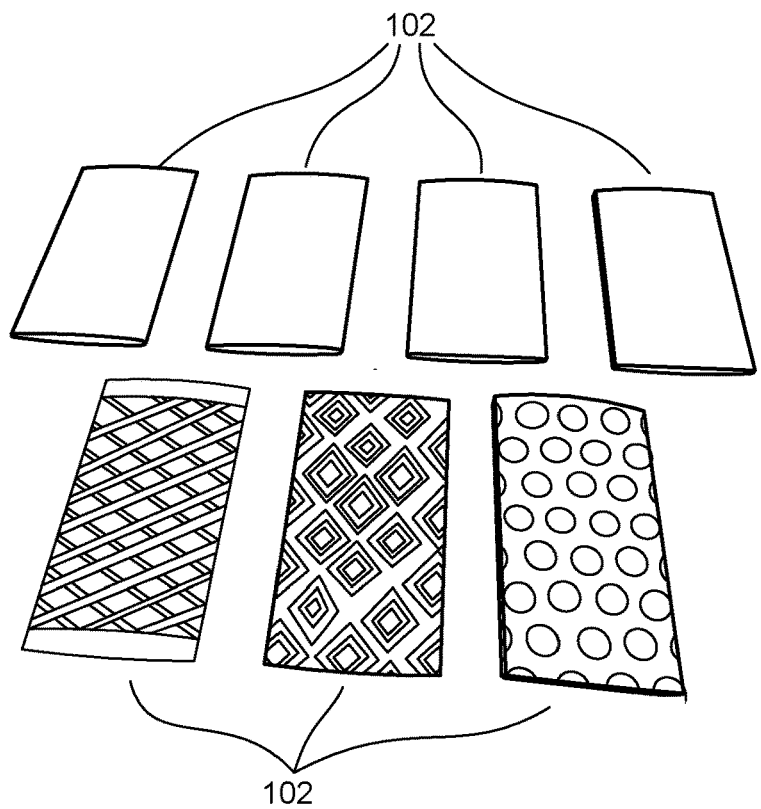
FIG. 11 is a photographic image of multiple skin-tone units of fabric sleeves as well as multiple decorative units in accordance with an embodiment of the present disclosure.

FIG. 11 is a photographic image of multiple skin-tone units of fabric sleeves 102 as well as multiple decorative units in accordance with an embodiment of the present disclosure. In some instances, sleeves 102 may be worn effectively as fashion statements.

Figure 12:
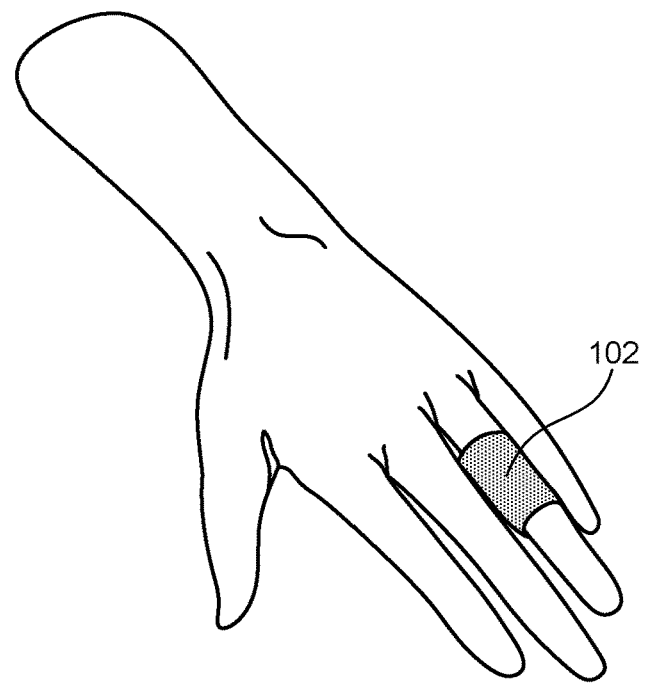
FIG. 12 is a photographic image of a human hand with a fabric sleeve one one of the fingers of the hand in accordance with an embodiment of the present disclosure.

FIG. 12 is a photographic image of a human hand with a fabric sleeve 102 on one of the fingers of the hand in accordance with an embodiment of the present disclosure.

The components, which together may be marketed with a product name such as "Sandal Toes", as provided herein may allow users to wear various styles of footwear without revealing blemishes that may be present on their feet. Users may be able to wear open-toe shoes such as peep-toes, sandals, gladiators, and flip-flops/thongs without blemishes being visible.

The sleeve may be made of at least one of nylon, spandex, cotton, acrylic, polyester, rayon, and other woven materials. The sleeve may be made in decorative designs that may include non-skin color shades and may include designs, implements, images, and decorative patterns. The sleeves may be made in various lengths and diameters and may be cut by users to accommodate individual toe and finger lengths. In an embodiment, only one unit of the sleeve may be included in packaging and the user may cut the unit to individual sizes.

The sleeves can be made in variations that function as a bandage, in which an absorbent pad would be included in the interior of the structure to cover and protect wounds on the toes. Padding can be produced from various materials to include but not limited to cotton and/or a water-absorbing gel. Said padding may or may not feature a thin, porous-polymer coating to keep it from sticking to a wound.

In variations of the sleeves that include padding, medications and/or antiseptic solution can be embedded into said padding for the treatment of various topical podiatric conditions, such as but not limited to corns, callouses, warts, blisters and other conditions.

The sleeves can be made in variations in which medicated pads, intended for individual application upon particular foot maladies prior to final application of the sleeves, may be included separately in packaging of the product. The sleeves can be made in reusable and/or disposable formats.

The applicator and the cylinder may each be produced in various shapes of applicability, and produced in various sizes. Each may be produced of various material such as but not limited to plastics such as high-density polyethylene (HDPE), polyamide-imide (PAI), polychlorotrifluoroethylene (PCTFE), nylon polyamide (PA), polycarbonate (PC), and acrylonitrile butadiene styrene (ABS).

Individual units of sleeves may vary in length, and may have an interior diameter of approximately one-half inch. This interior diameter can expand by stretching of the pliant material in order to fit individual toes/fingers. The storage cylinders are approximately two-inches (2") long and approximately ⅜" in diameter.

The applicator is approximately 2" in length. It is approximately ¼" in diameter at its narrowest point and ¾" at its widest. The narrowest point of the applicator is tubular in shape and fits within the hollow end of the storage cylinders.

The padding is produced of cotton covered with a thin, porous-polymer coating. The coating prevents the cotton padding from sticking to wounds and blemishes. The cotton padding is protected by the wax paper coating described above until time of use. Said wax paper features the extending tab as described above.

In units of the sleeves that feature flex bands, two flex bands may be featured in parallel, lengthwise alignment. The flex bands are produced in a convex shape out of woven spring band made of strands of flexible plastic. The fabric sleeves may be produced without padding and without flex bands, or with padding and without flex bands, or without padding and with flex bands, or with both padding and flex bands.

The sleeves may allow these users to wear popular footwear styles they ordinarily avoid in order to refrain from displaying the condition of their toes and may improve the composure and self-confidence of its users. Visibility may be eliminated of foot maladies that ordinarily make persons uncomfortable in social environments where such foot conditions may be visible to others.

The sleeves may allow users to enter and engage in many social environments in which such footwear is common and may allow users to better enjoy participating in such social environments. The sleeves eliminate the personal, social discomfort to which a consumer with foot maladies are ordinarily subject to while wearing such footwear.

The sleeves eliminate the personal, social discomfort to which a consumer with foot maladies are ordinarily subject to while wearing such footwear, and can expand the footwear options of a person with corns, calluses, warts, or blisters, who might ordinarily feel limited to closed shoes. They may give users confidence to select shoe styles of personal choice.

The sleeves eliminate the personal, social discomfort to which a consumer with foot maladies are ordinarily subject to while wearing such footwear. Systems provided herein are safer to use in response to corns, calluses, warts, and blisters than are other methods, such as surgery and medications.

The sleeves may be less expensive to use in response to corns, calluses, warts, and blisters than are other methods, such as surgery and medications. The sleeves can even protect users with corns, calluses, warts, and blisters from additional pain caused by those foot maladies.

The sleeves may protect blisters from being opened due to ordinary, unprotected contact to which they may be subject while shoes are worn. The sleeves may prevent corns and calluses from having direct and abrasive contact with other items, which can be painful and even make their conditions worse.

The sleeves may prevent warts from having direct and abrasive contact with other items, which can cause said warts to expand and bleed. The sleeves may protect shoe materials from stains and damages that can occur due to contact with pus and/or blood released from blisters and/or warts. The seamless construction of the sleeves may eliminate any abrasion upon the wearer that might ordinarily occur due to contact with seams. The seamless construction of the sleeves may also help with discreet wear of the product as non-straight seams are easily noticeable.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing a design for a system of applying sleeves to toes and fingers wherein blemishes are located according to the present invention will be apparent to those skilled in the art. Various aspects of the invention have been described above by way of illustration, and the specific embodiments disclosed are not intended to limit the invention to the particular forms disclosed. The particular implementation of the design for applying sleeves may vary depending upon the particular context or application. By way of example, and not limitation, the system of applying stretchable sleeves via rolling the sleeves from a cylinder to an applicator and onto the finger or toes may lend itself, however, to similar techniques that may instead be applied to any type of sleeve-like material that is stored in a rolled state that must be applied to a narrow and possibly cylindrical object, which is not limited to fingers and toes. Such implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

What is claimed is:

1. A system, comprising:
    a medicated columnar sleeve of stretchable fabric, the sleeve produced in various skin tone colors and configured to slip upon an individual toe or finger;
    absorbent padding configured for attachment to an inside surface of the sleeve, the padding configured to cover about one half of an interior circumference of the inside surface, the padding optionally infused with at least one of pain killers, antiseptics, and soothing gels;
    wax paper covering the padding prior to use of the sleeve;
    an applicator shaped to facilitate slipping the sleeve upon the individual toe or finger; and
    convex-shaped flex bands placed lengthwise into the sleeve.

2. The system of claim 1, whereby the flex bands exert downward pressure on one of a toe and a finger.

3. The system of claim 2, whereby the flex bands promote the sleeve to be placed in a U-shape, thus promoting the downward pressure.

4. The system of claim 3, whereby the sleeve is configured to conceal blemishes.

5. The system of claim 4, whereby the blemishes concealed by the sleeve comprise at least one of corns, calluses, warts, scars and blisters.

6. The system of claim 5, whereby the sleeve, prior to being slipped upon a toe or finger, is configured for storage in a rolled state.

7. The system of claim 6, whereby the sleeve is stored in the rolled state on a storage cylinder with a plurality of substantially identical sleeves.

8. The system of claim 7, whereby the storage cylinder is configured to connect to the applicator.

9. The system of claim 8, whereby the applicator is cone shaped.

10. The system of claim 9, whereby a narrow end of the applicator is configured to connect to the storage cylinder.

11. The system of claim 10, whereby a wide end of the applicator is configured to fit over one of the toe and the finger upon which sleeve is to be slipped.

12. The system of claim 2, whereby the downward pressure exerted by the flex bands at least one of which help stop bleeding.

13. The system of claim 12, whereby the downward pressure exerted by the flex bands further helps reduce and/or eliminate bulging puffiness of blemishes.

14. The system of claim 13, whereby, the sleeve is constructed without seams and without hems.

15. The system of claim 1, whereby the padding is configured to provide comfort and cushioning and protect toe/finger blemishes.

16. The system of claim 15, whereby the padding is further configured to absorb one of blood and other bodily fluid excreted from the blemishes.

17. The system of claim 16, whereby the wax paper is configured with an extending tab.

18. The system of claim 17, whereby the extending tab facilitates gripping and removal of the wax paper.

19. A system consisting of:
    a medicated columnar sleeve of stretchable fabric, the sleeve produced in various skin tone colors and configured to slip upon an individual toe or finger;
    absorbent padding configured for attachment to an inside surface of the sleeve, the padding configured to cover about one half of an interior circumference of the inside surface, the padding optionally infused with at least one of pain killers, antiseptics, and soothing gels;
    wax paper covering the padding prior to use of the sleeve;
    an applicator shaped to facilitate slipping the sleeve upon the individual toe or finger; and
    convex-shaped flex bands placed lengthwise into the sleeve,
    whereby the flex bands exert downward pressure on one of a toe and a finger,
    whereby the flex bands promote the sleeve to be placed in a U-shape, thus promoting the downward pressure,
    whereby the sleeve is configured to conceal blemishes,
    whereby the blemishes concealed by the sleeve comprise at least one of corns, calluses, warts, scars and blisters,
    whereby the sleeve, prior to being slipped upon a toe or finger, is configured for storage in a rolled state,
    whereby the sleeve is stored in the rolled state on a storage cylinder with a plurality of substantially identical sleeves,
    whereby the storage cylinder is configured to connect to the applicator,
    whereby the applicator is cone shaped,
    whereby a narrow end of the applicator is configured to connect to the storage cylinder,
    whereby a wide end of the applicator is configured to fit over one of the toe and the finger upon which sleeve is to be slipped,
    whereby the padding is configured to provide comfort and cushioning and protect toe/finger blemishes,
    whereby the padding is further configured to absorb one of blood and other bodily fluid excreted from the blemishes,
    whereby the wax paper is configured with an extending tab, whereby the extending tab facilitates gripping and removal of the wax paper, whereby the downward pressure exerted by the flex bands at least one of helps stop bleeding, whereby the downward pressure exerted by the flex bands further helps reduce and/or eliminate bulging puffiness of blemishes, and whereby, the sleeve is constructed without seams and without hems.

\* \* \* \* \*